US008808762B2

(12) United States Patent
Belkind et al.

(10) Patent No.: US 8,808,762 B2
(45) Date of Patent: *Aug. 19, 2014

(54) CINNAMALDEHYDE AND DIALLYL DISULFIDE FORMULATIONS AND METHODS OF USE

(71) Applicant: Valent BioSciences, Corporation, Libertyville, IL (US)

(72) Inventors: Benjamin A. Belkind, Libertyville, IL (US); Bassam Shammo, Libertyville, IL (US); Rebecca Dickenson, Libertyville, IL (US); Linda A. Rehberger, Libertyville, IL (US); Daniel F. Heiman, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/624,315

(22) Filed: Sep. 21, 2012

(65) Prior Publication Data

US 2013/0018107 A1    Jan. 17, 2013

Related U.S. Application Data

(63) Continuation-in-part of application No. 12/580,391, filed on Oct. 16, 2009, now Pat. No. 8,273,389.

(60) Provisional application No. 61/106,186, filed on Oct. 17, 2008.

(51) Int. Cl.
*A61K 36/00* (2006.01)
*A61K 36/54* (2006.01)
*A61K 36/8962* (2006.01)
*A61K 36/48* (2006.01)

(52) U.S. Cl.
USPC ............ 424/739; 424/754; 424/757; 424/776

(58) Field of Classification Search
None
See application file for complete search history.

(56) References Cited

U.S. PATENT DOCUMENTS

| 4,080,191 | A | 3/1978 | Harvey | ..................... 504/155 |
| 5,051,255 | A | 9/1991 | Devidas et al. | |
| 5,057,141 | A | 10/1991 | Rodriquez-Kabana et al. | |
| 5,182,207 | A | 1/1993 | Ward et al. | |
| 5,360,607 | A | 11/1994 | Eyal et al. | |
| 5,439,934 | A | 8/1995 | Wood et al. | |
| 6,231,865 | B1 | 5/2001 | Hsu et al. | |
| 6,251,951 | B1 | 6/2001 | Emerson et al. | |
| 6,348,434 | B1 | 2/2002 | Schmidt | |
| 6,750,256 | B1 | 6/2004 | Crandall, Jr. et al. | |
| 7,019,036 | B2 | 3/2006 | Hiromoto et al. | |
| 2001/0055628 | A1 | 12/2001 | Hsu et al. | |
| 2003/0005484 | A1 | 1/2003 | Crandall, Jr. et al. | |
| 2004/0127362 | A1 | 7/2004 | Hiromoto | |
| 2004/0235668 | A1 | 11/2004 | Abribat et al. | |
| 2005/0038094 | A1 | 2/2005 | Warrington | ............... 514/383 |
| 2007/0042182 | A1* | 2/2007 | Markus et al. | ............ 428/402.2 |
| 2008/0193387 | A1 | 8/2008 | De Wolff | |
| 2008/0274072 | A1* | 11/2008 | Manolas et al. | ............ 424/76.9 |
| 2009/0169655 | A1* | 7/2009 | Porter et al. | ................. 424/739 |
| 2010/0098787 | A1 | 4/2010 | Belkind et al. | |

FOREIGN PATENT DOCUMENTS

| DE | 3638290 A | 5/1988 |
| EP | 379851 A1 | 8/1990 |
| EP | 945066 A1 | 9/1999 |
| GB | 1 465 533 | 2/1977 |
| GB | 1465533 A * | 2/1977 |
| WO | WO 99/52359 | 10/1999 |
| WO | WO 99/56544 | 11/1999 |
| WO | WO 2012/123408 | 9/2012 |

OTHER PUBLICATIONS

Wikipedia on-line-dictionary.*
Extended European Search Report issued Jun. 10, 2013.
Block, "The organosulfur chemistry of the genus *Allium*—implications for the organic chemistry of sulfur", Angew. Chem. Int. Ed. Engl. 1992, 31, pp. 1135-1178.
Y.Oka, "Nematicidal activity of essential oil components against the root-knot nematode *Meloidogyne javanica*", Nematology, 2001, vol. 3(2), pp. 159-164.
R. Pandy et al., "Essential oils as potent sources of nematicidal compounds", J. Phytopathology 148, 2000, pp. 501-502.
Australian Pesticides & Veterinary Medicines Authority Guidelines for the Generation of Storage Stability Data of Agricultural Chemical Products, Dec. 2005, pp. 1-32.
Lima et al., "Evaluation of emulsifier stability of biosurfactant produced by *Saccharomyces* lipolytica CCT-0913", Brazilian Archives of Biology and Technology, vol. 52. N. 2, pp. 285-290m Mar.-Apr. 2009.
Lo et al., "Effects of surfactants on the emulsion stability of insecticide parathion emulsifiable concentrates in hard water", Journal of the Chinese Agricultural Chemical Society, Mar. 1989, 27(1), pp. 57-63.

* cited by examiner

*Primary Examiner* — Chris R Tate
*Assistant Examiner* — Deborah Davis
(74) *Attorney, Agent, or Firm* — Wood, Phillips, Katz, Clark & Mortimer

(57) ABSTRACT

The present invention relates to agricultural emulsion concentrates which form stable oil-in-water emulsions when diluted with water. More specifically, the invention relates to stable oil-in-water emulsions which include cinnamaldehyde and diallyl disulfide with a Calsogen® EH and Surfonic® CO 36 emulsion system. The increased stability of the emulsion allows for efficient mixing of the emulsion ingredients and effective storage and application of the cinnamaldehyde and diallyl disulfide to areas in need of nematode protection or treatment.

15 Claims, No Drawings

CINNAMALDEHYDE AND DIALLYL DISULFIDE FORMULATIONS AND METHODS OF USE

PRIORITY

This Application is a Continuation-in-Part of U.S. patent application Ser. No. 12/580,391, filed Oct. 16, 2009, and issued as U.S. Pat. No. 8,273,389, which claims the benefit of U.S. Provisional Application No. 61/106,186, filed Oct. 17, 2008, the contents of each are herein incorporated by reference.

FIELD OF THE INVENTION

The present invention relates to stable emulsions containing cinnamaldehyde and diallyl disulfide. Specifically, the stable emulsions utilize Emulsogen® EH and Surfonic® CO 36 to form a superior emulsion stability system.

BACKGROUND OF THE INVENTION

Emulsions generally refer to heterogeneous systems that comprise two immiscible liquids. In agriculture, emulsions provide formulation vehicles for delivery of herbicides, insecticides, fungicides, bactericides, and fertilizers.

Mechanical agitation, such as shaking or stirring, or another energy input is required to form an emulsion. Emulsions are inherently unstable, meaning that once they are formed, the immiscible liquids tend to revert or separate. Emulsifying agents, such as surface-active agents, can be used to increase the stability of the emulsions. In the context of emulsions, "stable" or "stability" means that the droplet particles of one liquid are uniformly distributed into another liquid and that this status is maintained for a desirable amount of time.

Emulsions are especially useful in the field of agriculture wherein numerous lipophilic active ingredients must be dissolved and suspended into water prior to application to the plants. An oil-in-water emulsion (O/W emulsion) is an emulsion wherein liquid oil droplets are finely dispersed in water. Preparing stable O/W emulsions in very difficult and frequently involves extensive experimentation to determine formulations that provide stable concentrated products for end-use diluted emulsions.

The emulsion system plays an essential role in providing stable emulsions, but identification of a proper system is complex and not easy to identify because of the required optimization of many different formulation characteristics, such as interfacial tension, viscosity, relative density, and temperature.

In addition, there are hundreds of different emulsifiers and surfactants commercially available with vastly different properties. The available emulsifiers and surfactants could be used in formulations in varying combinations and amounts to produce thousands of different potential formulations, each producing unpredictable stability characteristics. When more than one emulsifier or surfactant are combined in a formulation, they produce an emulsion system.

Calsogen® EH (available from Clariant) is an emulsifier, specifically, an iso-C12 alkyl benzene sulphonate calcium salt.

Surfonic® CO 36 (available from Huntsman, Inc.) is a surfactant and it contains polyglycol esters of castor oil.

Cinnamaldehyde is a naturally occurring organic compound that can be derived from the bark of trees of the genus *Cinnamomum*. Cinnamaldehyde is a viscous oil that has low solubility in water. Cinnamaldehyde does not present any known risk to humans or the environment and is considered to have a minimal safety risk. For this reason, it is not regulated by the Environmental Protection Agency ("EPA") because it is exempt from the Federal Insecticide, Fungicide, and Rodenticide Act ("FIFRA"). See 40 C.F.R. §152.25(f).

Cinnamaldehyde is known to have pesticidal activity. For example, cinnamaldehyde is effective against nematodes. See, for example, U.S. Pat. No. 6,251,951 B1.

Diallyl disulfide (4,5-dithia-1,7-octadiene) is a naturally occurring organosulfur compound that can be derived from garlic and plants of the genus *Allium*. Diallyl disulfide is an oil that has low solubility in water. Diallyl disulfide does not present any known risk to humans or the environment and is considered to have a minimal safety risk. For this reason, it is not regulated by the Environmental Protection Agency ("EPA") because it is exempt from the Federal Insecticide, Fungicide, and Rodenticide Act ("FIFRA"). See 40 C.F.R. §152.25(f).

There is a need to improve the safety characteristics of pesticides that are applied to plants intended for human and animal consumption. In order to achieve the goal of providing a safer pesticide, users must: (1) use environmentally safe actives, such as essential oils; and (2) if using essential oils, then they must include an environmentally safe emulsion system.

In prior art formulations, the use of environmentally harmful organic, solvents or other components were required to produce stable and effective dilutable emulsions if they contained plant essential oils, such as cinnamaldehyde and dially disulfide. Although organic solvents are very effective in forming emulsions, they are also often flammable, corrosive or toxic to living systems and are of environmental concern. For example, ProGuard® 30% is a commercially available insecticide, miticide and fungicide that contains cinnamaldehyde. However, ProGuard® 30% also contains the undesirable ingredient o-Phenylphenol.

Therefore, there is a need for environmentally safe pesticidal formulations that contain effective but safe actives.

SUMMARY OF THE INVENTION

Applicants unexpectedly discovered that an emulsion system comprising Emulsogen® EH and Surfonic® CO 36 provided excellent emulsion stability for cinnamaldehyde and diallyl disulfide formulations.

In one aspect, the invention is directed to improved and stable formulations containing *cinnamaldehyde* and diallyl disulfide with the emulsion system of Emulsogen® and Surfonic® CO 36.

In another aspect, the invention is directed to a specific agricultural formulation comprising about 61.0% cinnamaldehyde about 6.0 to about 8.5% diallyl disulfide, from about 13.0 to about 15.5% soybean oil, about 7.0% Calsogen® EH, and about 10.5% Surfonic® CO 36.

In a further aspect, the invention is directed to methods for suppressing plant damage by plant pathogens comprising applying the formulations of the invention to the locus, soil or seeds of plants in need of said treatment.

In a final aspect, the invention is directed to agricultural formulations comprising a synergistic amount of cinnamaldehyde and diallyl disulfide.

DETAILED DESCRIPTION in one embodiment of the invention, the invention is an agricultural formulation comprising cinnamaldehyde, diallyl disulfide, Surfonic® CO 36, and an iso-C12 alkylbenzene sulphonate calcium salt.

In another embodiment, the iso-C12 alkyl benzene sulphonate calcium salt is Calsogen® EH. In a further embodiment, the formulation may contain from about 5 to about 9% by weight of the iso-C12 alkyl benzene sulphonate calcium salt or Calsogen® EH, preferably from about 6.0 to about 8.0%, and most preferably about 7.0% of the iso-C12 alkyl benzene sulphonate calcium salt or Calsogen® EH.

In a further embodiment, the formulation may contain a lipophilic solvent. In a preferred embodiment, the lipophilic solvent is soybean oil. The formulation may contain from about 10.0 to about 20.0% by weight, preferably from about 12.0 to 16.0%, and most preferably from about 13.0 to about 15.5% of the lipophilic solvent or soybean oil.

In yet another embodiment, the formulation may contain from about 50 to about 70% by weight of cinnamaldehyde, preferably from about 58 to about 63% of cinnamaldehyde, and most preferably about 61% cinnamaldehyde.

In a further embodiment, the formulation may contain from about 5 to about 10% by weight of diallyl disulfide, preferably from about 5.5 to about 9.0%, and most preferably about from about 6.0 to about 8.5% of diallyl disulfide.

The formulation may contain from about 8 to about 12% of Surfonic® CO 36 by weight in one embodiment. Preferably, the formulation contains from about 9.0 to about 11.0% of Surfonic® CO 36, and more preferably, about 10.5% of Surfonic® CO 36.

In a preferred embodiment, the invention is directed to an agricultural formulation comprising: from about 59.5 to about 61.5% cinnamaldehyde; from about 6.0 to about 8.5% diallyl disulfide from about 13.0 to about 15.5% soybean oil; about 7.0% Calsogen® EH; and about 10.5% Surfonic® CO 36. In a more preferred embodiment, the formulation contains about 61.0% cinnamaldehyde.

An alternative embodiment is directed to methods for suppressing plant damage by plant pathogens comprising applying the formulation of the present invention to the locus, soil or seeds of plants in need of said treatment, in a preferred embodiment, the plant pathogens are nematodes.

In U.S. patent application Ser. No. 12/580,391, Applicants discussed the synergy between cinnamaldehyde and diallyl disulfide (see Example 3). Specifically, Applicants revealed that when cinnamaldehyde and diallyl disulfide are combined, nematodes are suppressed at bio-control levels far below those needed when the each component is applied alone. Applicants unexpectedly found that this effect was more than merely additive and was synergistic. Accordingly, in an embodiment, this invention is directed to agricultural formulations which contain a synergistic amount of cinnamaldehyde and diallyl disulfide.

The emulsifying system utilized in formulations of the present invention is a unique combination of two emulsifiers, Calsogen® EH and Surfonic® CO 36. This system can be used in the formulation with a total % weight from about 10 to about 30% of the formulation, preferably from about 15 to about 19% of the formulation, and most preferably at about 17.5% of the formulation.

As mentioned above, formulations of the present invention may contain lipophilic solvents. The preferred solvent is soybean oil, however, other solvents may be used as long as the solvents are "environmentally safe," meaning that they are exempt from volatile organic compound ("VOC") regulation by the EPA. For example, the following solvents may be used: methyl oleate, ethyl lactate, and methyl soyate. The agricultural formulations of the present invention explicitly exclude organic solvents which are considered to have unsatisfactory VOC levels as defined by California Environmental Protection Agency. The agricultural formulations of the present invention explicitly exclude ingredients which are considered by the state of California to cause cancer or reproductive toxicity under the The Safe Drinking Water and Toxic Enforcement Act of 1986 (see Health and Safety Code Section 25249.8(b)).

Formulations of the present invention contain an iso-C12 alkyl benzene sulfonate calcium salt. As previously mentioned, Calsogen® EH is preferred. However, other iso-C12 alkyl benzene sulfonate calcium salts known by those of skill in the art may be used in formulations of the invention, such as Phenylsulfonat CA or Phenylsulfonat CA 62 (both available from Clariant).

The trade names used herein are used to describe a type of component with specific chemistries. When a trade name is used herein, a component, with the same of very similar chemistry may be suitable unless indicated otherwise.

The terms "emulsion concentrate," "emulsifiable concentrate" and "formulation" are used interchangeably throughout the application.

The terms "emulsion system" and "emulsifying system" are used interchangeably throughout the application.

As used herein, all numerical values relating to amounts, weight percentages and the like, are defined as "about" or "approximately" each particular values plus or minus 10% (±10%). For example, the phrase "greater than 0.1%" is to be understood as encompassing values greater than 0.09%. Therefore, amounts within 10% of the claimed values are encompassed by the scope of the invention.

The percentages of the components in the formulations and comparative formulations are listed by weight percentage.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the active agents and excipients of the invention, may be made without departing from the spirit and scope hereof.

The following examples are offered by way of illustration only, not to limit the scope of this invention, as represented by the claims list attached herein.

EXAMPLES

Example 1

Preparation of a Cinnamaldehyde and Diallyl Disulfide Emulsion Concentrate Formulation A cinnamaldehyde and diallyl disulfide emulsion concentrate was prepared. The following components, in the amounts indicated below (in weight % of the component/total weight % of the formulation), were added in the order listed. The formulation was then mixed well with a magnetic stirrer until a homogeneous emulsion was formed.

61.0% cinnamaldehyde
21.5% diallyl disulfide and soybean oil (about 6 to 8.5% diallyl disulfide and 13.0 to
15.5% soybean oil)
7.0% Calsogen® EH
10.5% Surfonic® CO 36

The amount of diallyl disulfide added will vary depending upon the purity of the technical grade diallyl disulfide. Soybean oil may be used in varying amounts to accommodate the strength of the technical grade diallyl disulfide.

Example 2

Stability Study

The Formulation of Example 1 was compared with 16 other formulations containing the same amount of cinnamaldehyde, diallyl disulfide, and solvent but with different emulsifying systems. The 16 comparative emulsion concentrate formulations were prepared in a manner similar to the manner in which the Formulation of Example 1 was prepared as described above.

A standard emulsion stability test was utilized. Specifically, 5 mL of each emulsion concentrate formulation was added to 95 mL of water in a 100 mL graduated cylinder. The cylinder was stopped and inverted repeatedly until a homogeneous O/W emulsion was produced. The cylinder was then observed to detect phase separation or other indications of instability.

The results can be seen below in "Table 1. Emulsion Stability of Cinnamaldehyde and Diallyl Disulfide Formulations."

TABLE 1

Emulsion Stability of Cinnamaldehyde and Diallyl Disulfide Formulation

| Form. | Exp# | Emulsifying System | % in Form. | 0 min | 2 hr | 4 hr | 24 hr |
|---|---|---|---|---|---|---|---|
| Form. of Ex. 1 | 38C | Calsogen ® EH Surfonic ® CO 36 | 7 10.5 | Bloom: Excellent; Inversion: 0.5 | Emulsion: Excellent, uniform, thick; Separation: None | Emulsion: Excellent, uniform, thick; Separation: None | Emulsion: Excellent, uniform, thick; Separation: None |
| 2 | 38A | Calsogen ® EH Emulsogen ® EL 360 | 7 10.5 | Bloom: Excellent; Inversion: 0.5 | Emulsion: Excellent, uniform, thick; Separation: None | Emulsion: Good; Separation: 2 mL clear layer on bottom | Emulsion: Good; Separation: 4 mL clear yellow layer on bottom; Reconstitute: 0.5 inversion |
| 3 | 38B | Atlox ™ 4838B Emulsogen ® EL 360 | 7 10.5 | Bloom: Excellent; Inversion: 0.5 | Emulsion: Excellent, uniform, thick; Separation: None | Emulsion: Good; Separation: 1 mL clear layer on bottom | Emulsion: Good; Separation: 3 mL clear yellow layer on bottom; Reconstitute: 0.5 inversion |
| 4 | 38D | Atlas ™ G-1086 | 17.5 | Bloom: Unacceptable; Settling: Settled at 0 min; Inversion: 1 | Emulsion: Thinned out; Separation: 8.5 mL white precipitate on bottom. | Emulsion: Thinned out; Separation: 7 mL white precipitate on bottom. | Emulsion: Thinned out; Separation: 7 mL white precipitate on bottom. Reconstitute: 5 inversions |
| 5 | 38E | Atlox ™ 4838B Atlas ™ G-1086 | 7 10.5 | Bloom: Unacceptable; Settling: Settled at 0 min; Inversion: 1 | Emulsion: Thinned out; Separation: 6 mL white precipitate on bottom. | Emulsion: Thinned out; Separation: 2 mL yellow layer on bottom. | Emulsion: Thinned out; Separation: 3.5 mL yellow layer on bottom; Reconstitute: 0.5 inversion |
| 6 | 38F | Synperonic ® A20 | 17.5 | Bloom: Poor; Settling: Settled on bottom at 0 min; Inversion: 5 | Emulsion: Thinned out; Separation: 5 mL white precipitate on bottom. | Emulsion: None, top 10% clear; Separation: 5 mL white precipitate on bottom. | Emulsion: None; Separation: 5 mL white precipitate on bottom; Reconstitute: Did not in 5 inversions |
| 7 | 38G | Atlox ™ 4838B Synperonic ® A20 | 7 10.5 | Bloom: None, Unacceptable; Settling: Settled on bottom at 0 min; Inversion: 5 | Emulsion: Thinned out; Separation: 5 mL white on bottom. | Emulsion: Thinned out; Separation: 5 mL white on bottom. | Emulsion: Thinned out; Separation: 6 mL white precipitate on bottom; Reconstitute: Did not in 5 inversions |
| 8 | 38H | Calsogen ® EH Synperonic ® A20 | 7 10.5 | Bloom: None, Unacceptable; Settling: Settled on bottom at 0 min; Inversion: 5 | Emulsion: Thinned out; Separation: 5 mL white precipitate on bottom. | Emulsion: Thinned out; Separation: 5 mL white precipitate on bottom. | Emulsion: Thinned out; Separation: 7 mL white precipitate on bottom; Reconstitute: Did not in 5 inversions |
| 9 | 38I | Atlas ™ G-5000 | 17.5 | Bloom: Acceptable; Settling: Milky film on walls at 0 min; Inversion: 4 | Emulsion: Thinned out; Separation: 12 mL white precipitate on bottom. | Emulsion: Thinned out; Separation: 12 mL white precipitate on bottom. | Emulsion: Thinned out; Separation: 13 mL white precipitate on bottom; Reconstitute: Did not in 5 inversions |
| 10 | 38J | Atlox ™ 4838B Atlas ™ G-5000 | 7 10.5 | Bloom: Acceptable; Settling: Grit on | Emulsion: Thinned out; Separation: 10 mL white | Emulsion: Thinned out; Separation: 11 mL white | Emulsion: Thinned out; Separation: 12 mL white |

TABLE 1-continued

Emulsion Stability of Cinnamaldehyde and Diallyl Disulfide Formulation

| Form. | Exp# | Emulsifying System | % in Form. | 0 min | 2 hr | 4 hr | 24 hr |
|---|---|---|---|---|---|---|---|
| | | | | walls at 0 min; Inversion: 5 | precipitate on bottom, white film on walls. | precipitate on bottom, white film on walls | precipitate on bottom; Reconstitute: Did not in 5 inversions |
| 11 | 38K | Brij ® S20 | 17.5 | Bloom: None, Unacceptable; Settling: Settled on bottom at 0 min + grit; Inversion: 5, grit remains. | Emulsion: Thinned out; Separation: 5 mL white precipitate on bottom. | Emulsion: Thinned out; Separation: 5 mL white precipitate on bottom. | Emulsion: Thinned out; Separation: 5.5 mL white precipitate on bottom; Reconstitute: Did not in 5 inversions |
| 12 | 38L | Atlox ™ 4838B Brij ® S20 | 7 10.5 | Bloom: None, Unacceptable; Settling: Settled on bottom at 0 min + grit; Inversion: 5, grit gone. | Emulsion: Thinned out; Separation: 5 mL white precipitate on bottom. | Emulsion: Thinned out; Separation: 5 mL white precipitate on bottom. | Emulsion: Thinned out; Separation: 6 mL white precipitate on bottom; Reconstitute: Did not in 5 inversions |
| 13 | 38M | Tween ® 80 | 17.5 | Bloom: None, Unacceptable; Settling: Settled on bottom at 0 min; Inversion: 2 | Emulsion: Thinned out; Separation: 9 mL white precipitate on bottom. | Emulsion: Thinned out; Separation: 11 mL white precipitate on bottom. | Emulsion: Thinned out; Separation: 11 mL white precipitate on bottom; Reconstitute: Did not in 5 inversions |
| 14 | 38N | Atlox ™ 4838B Tween ® 80 | 7 10.5 | Bloom: Acceptable; Settling: None at 0 min; Inversion: 1 | Emulsion: Acceptable; Separation: 3 mL yellow layer on bottom. | Emulsion: Acceptable; Separation: 4 mL yellow layer on bottom. | Emulsion: Acceptable; Separation: 5 mL yellow layer on bottom; Reconstitute: 1 inversion |
| 15 | 38O | Calsogen ® EH Tween ® 80 | 7 10.5 | Bloom: Very good; Settling: None at 0 min; Inversion: 1 | Emulsion: Acceptable; Separation: 4 mL yellow layer on bottom. | Emulsion: Acceptable; Separation: 4 mL yellow layer on bottom. | Emulsion: Acceptable; Separation: 4 mL yellow layer on bottom; Reconstitute: 1 inversion |
| 16 | 38P | Tergitol ™ XD | 17.5 | Bloom: None, roping, Unacceptable; Settling: Settled on bottom at 0 min; Inversion: 5 | Emulsion: Poor; Separation: 9 mL precipitate on bottom. | Emulsion: None; Separation: 9 mL precipitate + 2 mL white layer above it, both on bottom. | Emulsion: None Separation: 9 mL precipitate + 3 mL white layer above it, both on bottom; Reconstitute: Did not in 5 inversions |
| 17 | 38Q | Calsogen ® EH Tergitol ™ XD | 7 10.5 | Bloom: Poor, Unacceptable; Settling: Settled on bottom at 0 min; Inversion: 2 | Emulsion: Thinned out; Separation: 5 mL precipitate on bottom. | Emulsion: Thinned out; Separation: 6 mL precipitate on bottom. | Emulsion: Thinned out; Separation: 7.5 mL precipitate on bottom; Reconstitute: Did not in 5 inversions |

In Table 1, the experimental properties of the emulsion are defined as follows: (a) "bloom" refers to the spontaneous visible dispersion and emulsification of the Emulsifiable Concentrate phase, when added into the water phase; (b) "inversion" refers to the number of times the cylinder was inverted to achieve an emulsion; (c) "separation" refers to the reversion of immiscible liquids into separate phases; (d) "thinned out" refers to the emulsion appearing thinner; (e) "reconstitute" refers to the number of inversion necessary to form an emulsion; (f) "settling" refers to the component which was deposited on the bottom of the cylinder; (g) "milky film" refers to a thick white film; and (h) "grit" refers to fine particulate-looking appearance.

Applicants unexpectedly discovered that the Formulation of Example 1 had superior stability, even after 24 hours. The Formulation of Example 1 quickly produced an emulsion. Throughout the observation period, the Formulation of Example 1 remained uniform and thick without separating. All of the other emulsion systems failed to produce satisfactory results. Achieving excellent stability after 24 hours is extremely rare in emulsion concentrate dilutions.

The unpredictability of the emulsion systems can be seen by comparing the stability of the Formulation of Example 1 with Formulation 2. Both formulations contained Calsogen® EH and the only difference between the formulations was that the Formulation of Example 1 contained Surfonic® CO 36 and Formulation 2 contained Emulsogen® EL 360. Surfonic® CO 36 and Emulsogen® EL 360 are both castor oil ethoxylates (36 EO), however, the Formulation of Example 1 had superior emulsion stability after 24 hours when compared to Formulation 2. Therefore, these formulations illustrate how emulsion systems with very similar chemistries may have different stability properties that cannot be predicted by one skilled in the art.

Further details regarding the alternative emulsion systems can be found below in "Table 2: Components in Emulsifying Systems."

TABLE 2

Components in Emulsifying Systems

| Trade Name | Chemistry |
|---|---|
| Calsogen ® EH | iso-C12 alkylbenzene sulphonate-calcium salt |
| Emulsogen ® EL 360 | Castor oil ethoxylate (36 EO) |
| Atlox ™ 4838B | Calcium alkylaryl sulphonate |
| Surfonic ® CO 36 | Castor oil ethoxylate (36 EO) |
| Atlas ™ G-1086 | Polyoxyethylene (40) sorbitol hexaoleate |
| Synperonic ® A20 | Polyoxyethylene (20) C12-C15 alcohol |
| Atlas ™ G-5000 | Polyalklene oxide block (EO/PO) copolymer |
| Brij ® S20 | Polyoxyethylene (20) oleyl ether |
| Tween ® 20 | Polyoxyethylene (20) sorbitan monooleate |
| Tergitol ™ XD | Alkyl EO/PO copolymer |

The invention claimed is:

1. An agricultural formulation comprising cinnamaldehyde, diallyl disulfide, from about 9 to about 12% of castor oil ethoxylated with 36 moles of ethylene oxide, and from about 5 to about 9% of an iso-C12 alkylbenzene sulphonate calcium salt.

2. The formulation of claim 1 further comprising a lipophilic solvent.

3. The formulation of claim 1 comprising from about 50 to about 70% of cinnamaldehyde.

4. The formulation of claim 1 comprising from about 5 to about 10% of diallyl disulfide.

5. The formulation of claim 2 comprising from about 10 to about 20% of the lipophilic solvent.

6. The formulation of claim 5 wherein the lipophilic solvent is soybean oil.

7. The formulation of claim 1 comprising from about 58 to about 63% of cinnamaldehyde.

8. The formulation of claim 1 comprising from about 7.0 to about 9.0% of diallyl disulfide.

9. The formulation of claim 1 comprising from about 6.0 to about 8.0% of iso-C12 alkylbenzene sulphonate calcium salt.

10. The formulation of claim 1 comprising from about 8.0 to about 11.0% of castor oil ethoxylated with 36 moles of ethylene oxide.

11. The formulation of claim 2 comprising from about 13.0 to about 15.5% of the lipophilic solvent.

12. An agricultural formulation comprising from about 59.5 to about 61.5% cinnamaldehyde; from about 6.0 to about 8.5% diallyl disulfide; from about 13.0 to about 15.5% soybean oil; about 7.0% iso-C12 alkylbenzene sulphonate calcium salt; and about 10.5% castor oil ethoxylated with 36 moles of ethylene oxide.

13. The formulation of claim 12 comprising about 61.0% cinnamaldehyde.

14. A method for suppressing plant damage by plant pathogens comprising applying the formulation of claim 1 to the locus, soil or seeds of plants in need of said treatment.

15. The method of claim 14 wherein the plant pathogen is a nematode.

* * * * *